(12) United States Patent  (10) Patent No.: US 8,012,664 B2
Zahn et al.  (45) Date of Patent: Sep. 6, 2011

(54) LIGHT-SENSITIVE COMPONENT FOR USE IN PHOTORESISTS

(75) Inventors: Wolfgang Zahn, Eltville (DE); Ralf Grottenmüller, Wiesbaden (DE); Dieter Wagner, Wiesbaden (DE)

(73) Assignee: AZ Electronic Materials USA Corp., Somerville, NJ (US)

( * ) Notice: Subject to any disclaimer, the term of this patent is extended or adjusted under 35 U.S.C. 154(b) by 67 days.

(21) Appl. No.: 12/084,614

(22) PCT Filed: Nov. 6, 2006

(86) PCT No.: PCT/EP2006/010607
§ 371 (c)(1), (2), (4) Date: May 5, 2008

(87) PCT Pub. No.: WO2007/051646
PCT Pub. Date: May 10, 2007

(65) Prior Publication Data
US 2009/0253073 A1    Oct. 8, 2009

(30) Foreign Application Priority Data
Nov. 7, 2005 (DE) .................... 10 2005 052 885

(51) Int. Cl.
*G03F 7/023* (2006.01)
*G03F 7/30* (2006.01)
*C07C 245/12* (2006.01)
(52) U.S. Cl. ........ 430/165; 430/192; 430/193; 430/326; 534/556; 534/557
(58) Field of Classification Search .......... 430/165, 430/192, 193, 326; 534/556, 557
See application file for complete search history.

(56) References Cited

U.S. PATENT DOCUMENTS 5,358,824 A * 10/1994 Tan et al. ............... 430/192
5,401,604 A * 3/1995 Otsuka et al. ............. 430/190

\* cited by examiner

*Primary Examiner* — John S Chu
(74) *Attorney, Agent, or Firm* — Sangya Jain

(57) ABSTRACT

A compound of the formula (I)

$$A\text{---}(E)_n\text{---}A' \quad (I)$$

where the symbols and indices are each defined as follows:
A is A', R or O—R; where R is a straight-chain, branched or cyclic, saturated or unsaturated aliphatic radical having 1-8 carbon atoms;
A' is the same or different and is

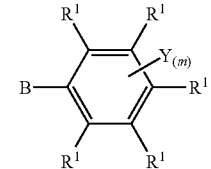

B is a bond, —O—C(O)—, —C(O)—O—, —O—C(O)—, —C(O)—NH—, —NH—C(O)—, —C(O)—O—CH$_2$—CH(OH)—CH$_2$—O, —O—CH$_2$—CH(OH)—CH$_2$—O—(O)C—, —O—C(O)—O—, —O—C(O)—NH— or —NH—C(O)—O—;
$R^1$ is H or OH;
m is 1, 2, 3, 4 or 5;
Y is

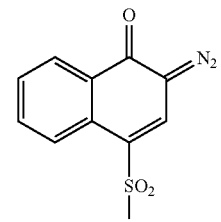

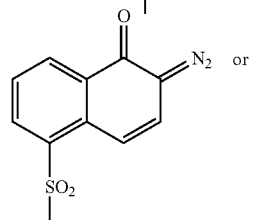

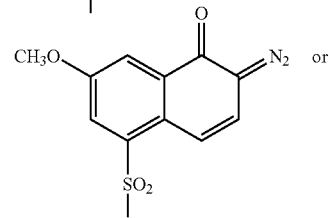

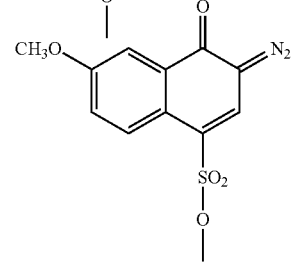

n is a positive rational number $\geq 3$;
E is the same or different and is —CH—CHR$^2$—, —CHR$^2$—CH$_2$—, —CH$_2$—CHR$^2$—O—, —O—CHR$^2$—CH$_2$—, —(CH$_2$)$_r$—O— or —O—(CH$_2$)—;
$R^2$ is H or CH$_3$ and
r is 1 or 4,
is suitable as a light-sensitive component for photoresists.

10 Claims, No Drawings

LIGHT-SENSITIVE COMPONENT FOR USE IN PHOTORESISTS

The invention relates to a light-sensitive oligo- or polymer which contains diazonaphthoquinonesulphonyl groups bonded to phenolic hydroxyl groups, to a process for its preparation and to its use as a light-sensitive component in photoresists.

Photoresists are used in lithographic processes, for example for the production of microelectronic components such as integrated circuits, computer chips and flat-panel displays. A known process for producing integrated circuits consists in (see, for example: DeForest, "Photoresist Materials and Processes", McGraw-Hill Book Company, New York, 1975), for example, coating a silicon wafer with a thin layer of a photoresist. The coated wafer is then baked in order to evaporate the solvent present in the photoresist and to fix the resist layer on the substrate. Subsequently, the coated substrate is exposed to irradiation through a photomask, which brings about a change in the chemical or physical properties of the resist layer. The radiation used is commonly light in the infrared region, visible light, UV light, X-radiation or an electron beam. After the irradiation, the coated substrate is treated with a so-called developer solution.

In the case of a positive photoresist (positive resist), the regions of the resist layer exposed to the radiation are dissolved and removed. When the photoresist is a negative resist, the unirradiated regions of the resist layer are dissolved and removed, and the irradiated regions remain. In the case of positive resists, the increase in the solubility in the course of illumination is often achieved by rearrangement reactions or by detachment of protective groups. In the case of negative resists, the decrease in the solubility in the course of illumination can be achieved, for example, by the occurrence of crosslinking reactions. In the regions in which the resist layer has been detached by the developing operation, the unprotected surface of the substrate is exposed and is then etched, for example with an etching solution or with a plasma treatment. The exposed surface can also be processed or manipulated, or its properties can be changed, in another way. The regions of the surface on which the resist layer is still present are not attacked by the etching operation. The remaining resist layer is now stripped completely from the substrate. What remains is a substrate surface on which an etched pattern is present, which corresponds to the photomask used in the illumination.

Known raw materials for positive resists which have proven useful in practice and are suitable particularly for illumination at wavelengths of 365 nm (i line), 405 nm (h line) and 436 nm (g line) have for many years been novolak resins, which are combined with diazonaphthoquinone functions. With these systems, it is possible to obtain structures having a resolution (line width) of about 0.25 µm. According to generally acknowledged theory, the combination of novolaks and diazonaphthoquinone functions works by virtue of the CO and $N_2$ moiety of the diazonaphthoquinones entering into pronounced hydrogen bonds with the phenolic OH groups of the novolak polymer, hence making them less amenable to the attack of the aqueous alkaline developer solution. This results in a significantly slowed layer attrition rate of a novolak/diazonaphthoquinone layer in the aqueous alkaline developer. After irradiation with light of suitable wavelength, the diazonaphthoquinone groups are converted photochemically to indenecarboxylic acid groups which no longer have any inhibiting action and even accelerate the rate of layer detachment somewhat.

The traditional way of obtaining novolak/diazonaphthoquinone combinations consists in mixing novolak resins with low molecular weight compounds containing phenolic OH groups, all or some of whose phenolic OH groups have been esterified with diazonaphthoquinonesulphonyl groups. These low molecular weight compounds are also known as "photosensitizers" or "PACs" (as an abbreviation for "Photo Active Compounds"), since they bear light-sensitive groups. A multitude of different compounds are already known as photosensitizers or PACs. Some structures are described hereinafter by way of example.

JP 1142548 describes a positive photoresist mixture which consists of a meta-/para-cresol novolak resin and a photosensitizer. The photosensitizer is an esterification product of a polyhydroxybenzophenone, such as 2,3,4-trihydroxybenzophenone or 2,3,4,4'-tetrahydroxybenzophenone, and 1,2-diazonaphthoquinone-4-sulphonic acid or 1,2-diazonaphthoquinone-5-sulphonic acid.

EP 0395049 A1 describes a positive photoresist formulation composed of an alkali-soluble novolak resin and a light-sensitive material. The light-sensitive material is a reaction product of 1,2-diazonaphthoquinone-5(or -4)-sulphonyl chloride and an aromatic polyhydroxyl compound. The aromatic polyhydroxyl compound has the structure Ar—X—Ar where Ar is a benzene ring having an OH group and one or two further substituents from the group of the alkyl or the alkoxy radicals. X is a difunctional moiety which may be —O—, —C(O)—, C(O)O—, —C(S)—, NHC(O)—, —NHC(O)O— or $C_1$-$C_4$-alkyl.

JP 10221846 describes a strictly linear novolak oligomer which consists of 4 para-cresol units which are bonded to formaldehyde exclusively via the positions ortho to the OH group. Partial or full esterification of the OH groups with diazonaphthoquinone groups gives rise to a light-sensitive component for photoresists.

In addition to the known way of obtaining novolak/diazonaphthoquinone combinations by mixing novolaks with photosensitizers or PACs, there is also the possibility of binding at least some of the diazonaphthoquinone groups directly to the phenolic OH groups of the high molecular weight novolak resin. In spite of this, it is generally still necessary to add low molecular weight photosensitizers or PACs.

According to the current state of the art, a multitude of different mixtures is known. Some mixtures are described hereinafter by way of example.

U.S. Pat. No. 5,529,880 and U.S. Pat. No. 5,723,254 describe a photoresist which is a mixture of a novolak resin in which up to a maximum of 20% of the OH groups have been esterified with diazonaphthoquinone groups, and an oligomeric phenol having 2 to 5 phenolic OH groups, of which at least 50% have been esterified with diazonaphthoquinone groups.

JP 2004 4029840 describes a photoresist which comprises, as an essential component, an alkali-soluble novolak resin in which some of the phenolic OH groups are present in the form of diazonaphthoquinone esters.

JP 59084239 describes a light-sensitive composition whose essential constituent is a novolak resin, some of whose phenolic OH groups have been esterified with diazonaphthoquinone groups.

In the processes currently used industrially, it is unavoidable to add low molecular weight PACs to photoresists. This also applies to the case that the diazonaphthoquinone groups are bonded directly to the novolak resin. This is because the light sensitivity (required minimum illumination energy for a change in solubility) is insufficient in such systems, so that a certain amount of PAC has to be added in any case. Particularly highly esterified PACs, however, exhibit a marked tendency to precipitate out or crystallize out of photoresist solutions after more or less prolonged standing. This phenomenon restricts the storage stability of photoresist solutions significantly and can lead to considerable problems in processing. Particles present on the coated wafer have significantly greater dimensions than the structures to be obtained and therefore make at least parts of the wafer unusable. In order to prevent this, a fine-pore filter is in practice inserted immediately before the coating operation, which frees the resist solution of particles. Excessive particle formation of a photoresist necessitates frequent and complicated change of the filter, and must therefore absolutely be prevented.

It is therefore an object of the invention to avoid said disadvantages of the prior art and in particular to provide photoresist solutions having a high storage stability.

It has now been found that oligo- or polymeric polyethers and polyolefins which have been modified terminally with diazonaphthoquinonesulphonyl units have, in addition to high light sensitivity, good solubility in organic solvents and a low tendency to precipitate out or crystallize out, and are thus outstandingly suitable as light-sensitive components for photoresists.

The invention therefore provides a compound of the formula (I)

$$A-(E)_n-A' \quad (I)$$

where the symbols and indices are each defined as follows:

A is A', R or O—R; where R is a straight-chain, branched or cyclic, saturated or unsaturated aliphatic radical having 1-8 carbon atoms;

A' is the same or different and is

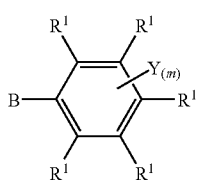

B is a bond, —O—C(O)—, —C(O)—O—, —O—C(O)—, —C(O)—NH—, —NH—C(O)—, —C(O)—O—CH$_2$—CH(OH)—CH$_2$—O, —O—CH$_2$—CH(OH)—CH$_2$—O—(O)C—, —O—C(O)—O—, —O—C(O)—NH— or —NH—C(O)—O—;

R$^1$ is H or OH;

m is 1, 2, 3, 4 or 5;

Y is

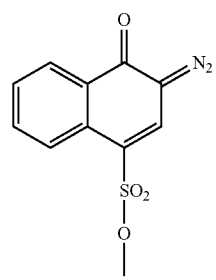 (II)

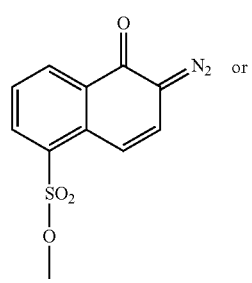 (III)

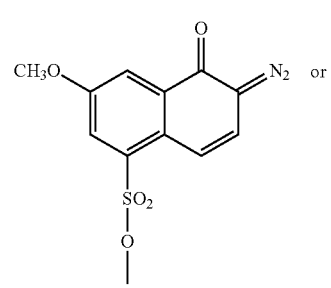 (IV)

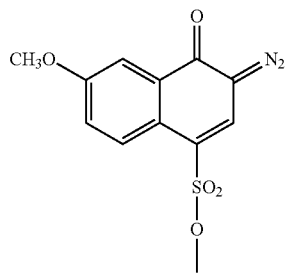 (V)

n is a positive rational number $\geq 3$;

E is the same or different and is —CH—CHR$^2$—, —CHR$^2$—CH$_2$—, —CH$_2$—CHR$^2$—O—, —O—CHR$^2$—CH$_2$—, —(CH$_2$)$_r$—O— or —O—(CH$_2$)—;

R$^2$ is H or CH$_3$; and r is 1 or 4.

Oligo- and polymers (referred to collectively hereinafter as polymers) of the formula (I) are, owing to their high light sensitivity, good solubility in organic solvents and low crystallization tendency, outstandingly suitable as a light-sensitive component in photoresists, especially positive resists.

The polymers of the formula (I) are homopolymers (the repeat unit E is identical) or copolymers (the repeat unit E has different structures E', E", etc.).

Copolymers of the formula (I) may, for example, be random copolymers (e.g. E'-E"-E'-E'-E"-E'-E"-E" ... ), alternating copolymers (-[E'-E"]-) or block copolymers (e.g. (E'-E'-E')(E"-E"-E")).

Preference is given to units E in the formula (I) which have branches and/or ether moieties; particular preference is given to the propylene glycol (—O—CH$_2$—CH(CH$_3$)—), ethylene glycol (—O—CH$_2$—CH$_2$—) and tetramethylene oxide (—O—(CH$_2$)$_4$—) units.

In general, the polymers of the formula (I) have a weight-average molecular weight (Mw) of 50 to 10 000, preferably 100 to 2500, more preferably 120 to 1500.

Since n is the average of the repeat units present in a polymer of the formula (I) (distribution), it may also have values other than whole numbers (e.g. 5.5).

The symbols and indices in the formula (I) are preferably each defined as follows:

A is preferably A', R or OR, where R is a straight-chain or branched (C$_1$-C$_8$)-alkyl group or (C$_3$-C$_8$)-cycloalkyl.

B is preferably a bond, —O—, —C(O)—O, —O—C(O)—, —C(O)—O—CH$_2$—CH(OH)—CH$_2$—O— or —CH$_2$—CH(OH)—CH$_2$—O—C(O)—.

R$^1$ is preferably H or OH.

m is preferably 2, 3 or 4.

Y is preferably (II)

[structure with N$_2$ or]

(III)

[structure with N$_2$·]

n is preferably a positive rational number ≧3 and ≦80.

E is preferably —CH$_2$—CHR$^2$—O—, —O—CHR$^2$—CH$_2$— or —(CH$_2$)$_r$—O—, —O—(CH$_2$)$_r$—.

R$^2$ is preferably H or CH$_3$.

r is preferably 1 or 4.

Preference is given to compounds of the formula (I) in which the symbols and indices each have the preferred definitions.

The symbols and indices in the formula (I) more preferably have the following definitions:

A is more preferably A', R or OR, where R is a straight-chain or branched (C$_1$-C$_8$)-alkyl group.

B is more preferably a bond, —O—, —O—C(O)—, —C(O)—O—, C(O)—O—CH$_2$—CH(OH)—CH$_2$—O or —CH$_2$—CH(OH)—CH$_2$—O—C(O).

R$^1$ is more preferably H or OH.

m is more preferably 2 or 3.

Y is more preferably (III)

[structure with N$_2$]

n is more preferably ≧5 and ≦20.

E is more preferably —CH$_2$—CH(CH$_3$)—O, —CH$_2$—CH$_2$—O, —O—CH$_2$(CH$_3$)—CH$_2$—, —O—CH$_2$—CH$_2$—, —CH(CH$_3$)—CH$_2$—O, —O—CH$_2$—CH(CH$_3$)— or (CH$_2$)$_4$—O— or —O—(CH$_2$)$_4$—.

Particular preference is given to compounds of the formula (I) in which the symbols and indices each have the more preferred definitions.

In particular, the symbols and indices in the formula (I) are each defined as follows:

A is in particular A', a straight-chain or branched (C$_1$-C$_4$)-alkyl group.

B is in particular a bond, —C(O)—O—, —O—C(O)—, C(O)—O—CH$_2$—CH(OH)—CH$_2$—O— or —CH$_2$—CH(OH)—CH$_2$—O—C(O)—.

R$^1$ is in particular H or OH.

m is in particular 2 or 3.

Y is in particular (III)

[structure with N$_2$·]

n is in particular ≧5 and ≦15.

E is in particular —O—CH$_2$—CH$_2$—, —CH$_2$—CH$_2$—O—, —O—CH(CH$_3$)—CH$_2$—, —O—CH$_2$—CH(CH$_3$)—, CH(CH$_3$)—CH$_2$—O— or —CH$_2$—CH(CH$_3$)—O—.

For E, particular preference is also given to a mixture of ethylene glycol and propylene glycol units.

Polymer units E$_n$ can be prepared by the known processes for preparing polyglycols, polyacetals and polyolefins, as described, for example, in the form of review articles in "Kirk-Othmer, Encyclopedia of Chemical Technology", 2004, 5th Edition, John Wiley & Sons.

These terminally modified or unmodified polymers are additionally commercially available. Polyethylene glycol bisglycidyl ethers and polypropylene glycol bisglycidyl ethers are sold, for example, by Nagase & Co. Ltd. (Tokyo, Japan), alkylpolyethylene glycols and alkylpolypropylene glycols, for example, by BASF Aktiengesellschaft (Ludwigshafen, Germany) or Clariant GmbH (Sulzbach, Germany).

The polymer precursor ($E_n$) is reacted with the aromatic component(s) A' (A'=A where m=0) by known methods of etherification, esterification or amidation, as specified, for example, in J. March, Advanced Organic Chemistry, 5th ed., John Wiley & Sons, New York 2001, pages 707-711 or H. Kotsoki, Synthesis 4 (1999), pages 603-606.

For example, alcohols or their methanesulphonates can be reacted with pyrogallol or other (poly)hydroxybenzenes.

The compounds of the formula (I) are synthesized subsequently in a known manner by reacting the corresponding precursors with 2,1-diazonaphthoquinone-4-sulphonyl chloride, 2,1-diazonaphthoquinone-5-sulphonyl chloride, 7-methoxy-2,1-diazonaphthoquinone-4- or -5-sulphonyl chloride and a base in an organic solvent. In general, two synthesis routes are possible. Firstly, the product can be isolated as solid by precipitation in an excess of water and if appropriate reprecipitation after drying. Secondly, the synthesis can be performed in an organic solvent with only limited water miscibility, if any. In that case, the purification is effected by washing with water, phase separation and subsequent incipient distillation of the organic phase which contains the product in dissolved form in order to remove residues of dissolved water.

The invention therefore also provides a process for preparing a compound of the formula (I) by reacting a compound of the formula (I)'
in which
A' is

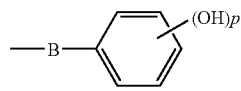

p is 1, 2, 3, 4 or 5
and the remaining symbols and indices are each as defined in formula (I),
in an organic solvent in the presence of a base, with at least one compound from the group of 2,1-diazonaphthoquinone-4-sulphonyl chloride, 2,1-diazonaphthoquinone-5-sulphonyl chloride, 7-methoxy-2,1-diazonaphthoquinone-4- and 5-sulphonyl chloride.

Preferred organic solvents are acetone, 2-butanone, γ-butyrolactone, 1,4-dioxane, propylene glycol monomethyl ether and propylene glycol monomethyl ether acetate.

Preferred bases are tertiary bases such as triethylamine, triethanolamine, methyldiethanolamine, dimethylethanolamine, pyridine, N-methylmorpholine, 1,4-diazabicyclo[2.2.2]octane and 1,8-diaza-bicyclo[5.4.0]undec-7-ene.

The invention further provides for the use of a compound of the formula (I) as a constituent of photoresists, preferably positive resists.

The invention likewise provides a photoresist composition, preferably a positive resist composition, comprising
  a) a light-sensitive component comprising one or more compounds of the formula (I) and
  b) a film-forming, base-soluble component.

The film-forming components used are generally novolak resins.

Useful novolak resins include all types which are obtainable by the commonly known (see, for example, A. Gardziella, L. A. Pilate "Phenolic Resins", 2nd edition, Springer Verlag, Berlin, 2000) acid- or else metal ion-catalysed condensation reaction from phenol or phenol derivatives and lower aldehydes or ketones. Useful phenol derivatives include, for example, phenol itself, cresol (1-, 2- or 3-methylphenol), o-, m- or p-alkylphenol, xylenol (2,3-, 2,4-, 2,5-, 2,6-, 3,4-, 3,5- or 3,6-dimethylphenol), o-, m- or p-phenylphenol, dialkylphenol, trialkylphenol, mono-, di- or trialkoxyphenol, pyrocatechol (1,2-dihydroxybenzene), resorcinol (1,3-dihydroxybenzene), hydroquinone (1,4-dihydroxybenzene), pyrogallol (1,2,3-trihydroxy-benzene), 1,2,4-trihydroxybenzene or phloroglucinol (1,3,5-trihydroxybenzene). These or other phenols may be used alone or in mixtures of two or more components. Useful aldehydes or ketones, which may be used individually or in combination, include, for example, formaldehyde, paraformaldehyde, trioxane, acetaldehyde, benzaldehyde, furfural, propionaldehyde, acrolein, crotonaldehyde, cyclohexylaldehyde, acetone, methyl ethyl ketone, diethyl ketone, diphenyl ketone, or other aldehydes or ketones. The synthesis of novolaks of all types from a wide variety of different monomers or monomer combinations is described in detail in numerous publications and patents and is commonly known prior art. The use of novolaks formed from specific monomers, with specifically adjusted molar mass or molar mass distribution, for example by removal of low molecular weight fractions by fractionation or by selective mixing of two or more novolaks with different molar masses, is likewise described (see, for example, U.S. Pat. No. 4,529,682, U.S. Pat. No. 6,096,477, WO 00/34829 and U.S. Pat. No. 3,666,473).

Preferred novolak resins are those which are obtained from the monomers phenol, cresol and xylenol in any mixtures by condensation with formaldehyde.

The proportion of the compound(s) of the formula (I) is typically 5 to 50 parts by weight, preferably 10 to 40 parts by weight, based on 100 parts by weight of the film-forming resin.

Preferred solvents for the photoresist composition are ethylene glycol monoalkyl ethers such as ethylene glycol monomethyl ether and ethylene glycol monoethyl ether, ethylene glycol monoalkyl ether acetates such as ethylene glycol monomethyl ether acetate and ethylene glycol monoethyl ether acetate, propylene glycol monoalkyl ethers such as propylene glycol monomethyl ether and propylene glycol monoethyl ether, propylene glycol monoalkyl ether acetates such as propylene glycol monomethyl ether acetate and propylene glycol monoethyl ether acetate, lactates such as methyl lactate and ethyl lactate, aromatic hydrocarbons such as toluene and xylenes, ketones such as methyl ethyl ketone, 2-heptanone and cyclohexanone, amides such as N,N-dimethylacetamide and N-methylpyrrolidone, lactones such as γ-butyrolactone, and acetates such as ethyl acetate, butyl acetate and 3-methoxybutyl acetate. These solvents may be used either individually or as a mixture of two or more thereof.

Particular preference is given to 1-methoxy-2-propyl acetate, 1-methoxy-2-propanol, ethyl lactate and butyl acetate.

The photoresist composition can optionally be admixed with further additives, for example a dye as an adhesion assistant. Examples of the dyes are methyl violet, crystal violet and malachite green; examples of adhesion assistants include alkylimidazolines, butyric acid, alkanoic acids, polyhydroxystyrenes, polyvinyl methyl ether, t-butyl novolak, epoxysilanes, epoxy polymers and silanes.

The photoresist composition can be prepared by dissolving the film-forming component, the compound of the formula (I) and optionally further additives in a predetermined amount of solvent and optionally filtering the mixture. The light-sensitive photoresist composition thus prepared is applied to a substrate to produce integrated semiconductor switching elements, photofilters and FPDs such as liquid-crystal displays. The substrates may be any substrates with any size, such as glass substrates and silicon substrates. They may also be those substrates which comprise a film, for example a chromium film, a silicon oxide film or an antireflection film. The substrate may be coated with the photoresist composition by any known process, for example by spin-coating, roll-coating, land-coating, flow- and spread-coating, doctor-coating, dip-coating and slit-coating.

The photoresist composition is applied to the substrate and then soft-baked in order to form a light-sensitive film. Thereafter, the film is illuminated through a photomask and developed by processes which are known and familiar to those skilled in the art in order to form a resist pattern. Preference is given to light of the wavelengths 365 nm, 405 nm and 436 nm.

The developer which is employed for the subsequent development may be any developer as used in conventional light-sensitive resin compositions. Preferred examples of the developer include basic developers, i.e. aqueous solutions of alkaline compounds such as tetraalkylammonium hydroxide, choline, alkali metal hydroxides, alkali metal metasilicates (hydrates), alkali metal phosphates (hydrates), ammonia solution, alkylamines, alkanolamines and heterocyclic amines; an aqueous solution of tetramethylammonium hydroxide is particularly preferred as an alkaline developer. If appropriate, the alkaline developer solutions may comprise water-soluble organic solvents such as methanol and ethanol, or surfactants. Development with the alkaline developer is commonly followed by washing with water.

The invention further provides a process for the structured coating of a substrate by
a) coating a substrate with a film of the inventive photoresist composition,
b) illuminating the photoresist film formed through a photomask,
c) baking the illuminated photoresist film and
d) developing the baked, illuminated photoresist film with an alkaline developer.

The invention likewise provides a substrate coated with the inventive photoresist composition, and its use in the production of semiconductor switching elements and flat-panel displays.

The invention is illustrated in detail by the examples without being restricted thereby.

EXAMPLES

For the examples below, the following precursors were used:

Precursor 1. Prepared by reacting 1 mol of polypropylene glycol bis(glycidyl ether) with 2 mol of gallic acid. n has a mean value of 7.

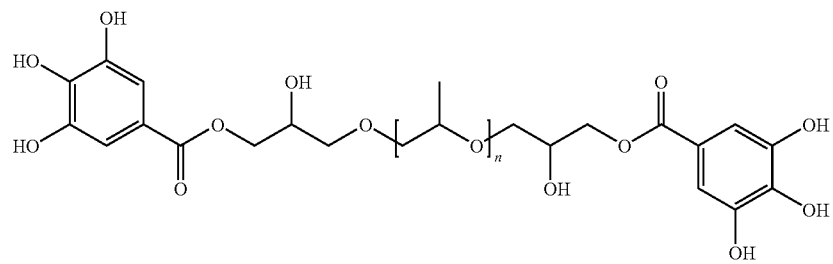

Precursor 2. Prepared by reacting 1 mol of polyethylene glycol bis(glycidyl ether) with 2 mol of gallic acid. n has a mean value of 9.

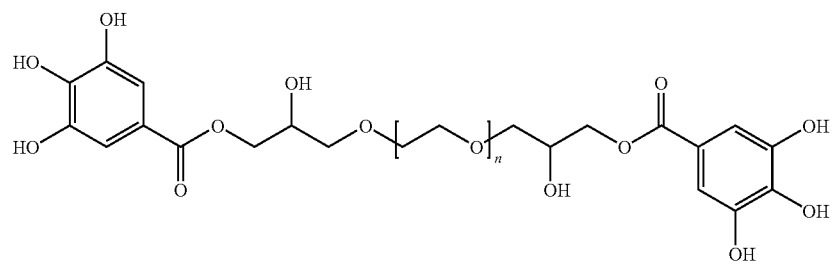

Precursor 3. Prepared by reacting 1 mol of polypropylene glycol bis(glycidyl ether) with 2 mol of 3,5-dihydroxybenzoic acid. n has a mean value of 7.

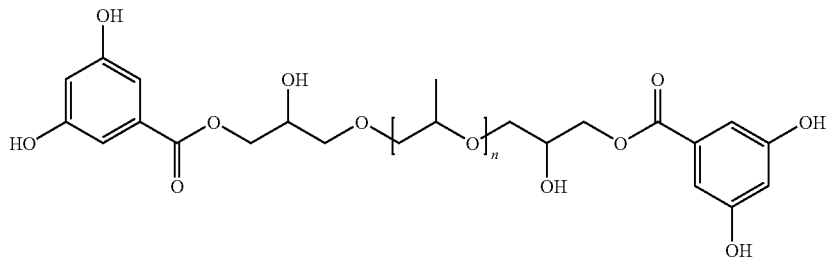

Precursor 4. Prepared by reacting 1 mol of polyethylene glycol bis(glycidyl ether) with 2 mol of 3,5-dihydroxybenzoic acid. n has a mean value of 9.

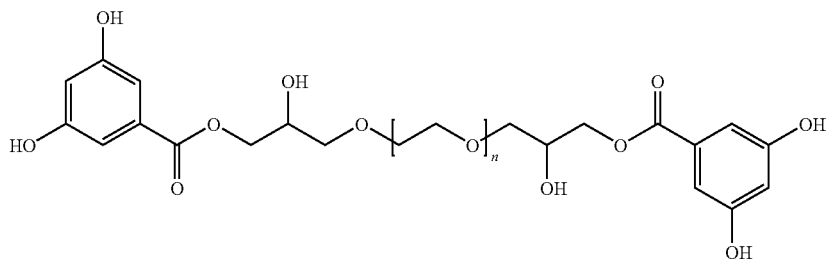

Precursor 5. Prepared by reacting 1 mol of polypropylene glycol bis(glycidyl ether) with 2 mol of 4-hydroxybenzoic acid. n has a mean value of 7.

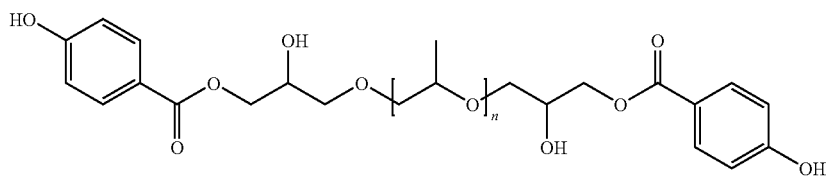

Precursor 6. Prepared by reacting 1 mol of pyrogallol with 1 mol of polypropylene glycol monomethyl ether. n has a mean value of 6.5.

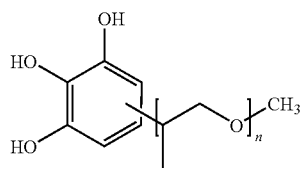

Precursor 7. Prepared by reacting 1 mol of pyrogallol with 1 mol of polyethylene glycol monomethyl ether. n has a mean value of 8.5.

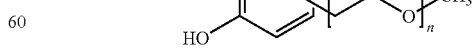

General method "A" for the esterification of the precursors with 2,1-diazonaphthoquinone-5-sulphonyl chloride and subsequent precipitation and drying of the product 1 mol of the appropriate precursor is dissolved in the molar ratio of 2,1-diazonaphthoquinone-5-sulphonyl chloride specified in Table 1 to give a clear 15% by weight solution in acetone. At a temperature of 15-20° C., 1.05 molar equivalents of triethylamine, based on moles of 2,1-diazonaphthoquinone-5-sulphonyl chloride, are added dropwise within 30 min and the mixture is stirred for a further 60 min. The solution is filtered to free it of precipitated ammonium hydrochloride and added dropwise slowly into 20 times the amount of 0.02% aqueous HCl. The precipitated product is filtered off with suction, washed thoroughly with deionized water, suction-dried and dried at 40° C. for 72 h until the water content is <1%. The product is obtained as a red-brown solid.

General method "L" for the esterification of the precursors with 2,1-diazonaphthoquinone-5-sulphonyl chloride in organic solvent without precipitation (the product is obtained as a solution)

1 mol of the appropriate precursor is dissolved in the molar ratio of 2,1-diazonaphthoquinone-5-sulphonyl chloride specified in Table 1 in a 9:1 mixture of 1-methoxy-2-propyl acetate and 1-methoxy-2-propanol to give a clear 15% by weight solution. At a temperature of 15-20° C., 1.05 molar equivalents of dimethylethanolamine, based on moles of 2,1-diazonaphthoquinone-5-sulphonyl chloride, are added dropwise within 30 min, and the mixture is stirred for a further 60 min. The reaction solution is then washed in a quantitative ratio of 1:1 with 0.3% aqueous HCl. After the aqueous phase has been removed, the organic phase is washed in a quantitative ratio of 1:1 with deionized water, and the aqueous phase is removed. The remaining organic phase is first incipiently distilled at 45° C. and a vacuum of 20 mbar for 60 min. The pressure is then reduced to 8 mbar and distillation is continued for a further approx. 60 min. What remains is a deep red solution of the product in 1-methoxy-2-propyl acetate (PGMEA) having a solids content of 30-40% by weight, which is determined accurately by analysis. The water content is <0.5%.

The compounds of the formula (I) listed in Table 1 were obtained.

TABLE 1

| Compound of the formula (I) | Precursor[1] | Moles of DNQ[2] | Synthesis[3] | SC[4] |
|---|---|---|---|---|
| Example 1 | 1 | 4.25 | A | 100% |
| Example 2 | 2 | 4.25 | A | 100% |
| Example 3 | 3 | 3.75 | A | 100% |
| Example 4 | 3 | 3.75 | L | 38.7% |
| Example 5 | 4 | 3.75 | A | 100% |
| Example 6 | 5 | 2.0 | A | 100% |
| Example 7 | 6 | 3.0 | A | 100% |
| Example 8 | 6 | 3.0 | L | 37.5% |
| Example 9 | 7 | 3.0 | A | 100% |

[1] 1 mol each
[2] DNQ: 2,1-diazonaphthoquinone-5-sulphonyl chloride
[3] A: by method "A" with precipitation and drying L: by method "L", prepared in solution
[4] SC: solids in % by weight, Example 4 and 8 dissolved in PGMEA The lithography process is performed as follows:

Ready-to-use resist solutions are first prepared from the PACs specified in Table 1 according to the formulation shown in Table 2. The PACs are dissolved together with the novolak resin and the additive to give a clear solution in PGMEA (1-methoxy-2-propyl acetate) and adjusted to a total solids content of 27% by weight. Immediately before use, the resist solutions are filtered through a 0.45 μm filter.

TABLE 2

| Resist | Compound of the formula (I) from:[1] Example | Comparative example | Amount of PAC | Resin[2] | PGMEA | Additive[3] | SC[4] |
|---|---|---|---|---|---|---|---|
| No. 1 | 1 | — | 3.6 g | 22.3 g | 70.7 g | 0.25 g | 27% |
| No. 2 | 2 | — | 4.0 g | 22.0 g | 71.0 g | 0.25 g | 27% |
| No. 3 | 3 | — | 5.4 g | 20.6 g | 70.1 g | 0.25 g | 27% |
| No. 4 | 4 | — | 14.0 g | 20.6 g | 61.5 g | 0.25 g | 27% |
| No. 5 | 5 | — | 3.8 g | 22.1 g | 70.7 g | 0.25 g | 27% |
| No. 6 | 6 | — | 6.5 g | 19.5 g | 71.0 g | 0.25 g | 27% |
| No. 7 | 7 | — | 5.8 g | 20.7 g | 72.3 g | 0.25 g | 27% |
| No. 8 | 8 | — | 15.5 g | 20.7 g | 62.6 g | 0.25 g | 27% |
| No. 9 | 9 | — | 6.3 g | 20.4 g | 72.9 g | 0.25 g | 27% |
| No. 10 | — | 1[1] | 5.2 g | 20.8 g | 70.9 g | 0.25 g | 27% |
| No. 11 | — | 2[1] | 4.8 g | 20.8 g | 71.3 g | 0.25 g | 27% |

[1] Examples 1-9: see Table 1
Comparative example 1: reaction product formed from 1 mol of 2,3,4,4'-tetrahydroxybenzophenone with 3.75 mol of 2,1-diazonaphthoquinone-5-sulphonyl chloride
Comparative example 2: reaction product formed from 1 mol of 2,3,4-trihydroxybenzophenone with 3.0 mol of 2,1-diazonaphthoquinone-5-sulphonyl chloride
[2] Resin: meta/para-cresol novolak having a molar mass of 7500 g/mol
[3] Additive: KP 341 (organosiloxane polymer from Shin-Etsu Chemical Co. Ltd.) as a wetting agent, 5% solution in PGMEA
[4] solids content of the dilution in percent by weight The resist solution is coated onto Si wafer by means of spin-coating, the spinning speed being adjusted such that a quite precise resist layer thickness around 1.5 μm (depending on the interference-related coupling-in of the illumination wavelength) is achieved after drying. After the coating, the wafer is baked on a controllable hotplate to remove the solvent under defined conditions. In general, drying is effected at a temperature of 90° C. for 60 s. Subsequently, the layer is illuminated with an illumination unit (wafer stepper) of a particular illumination wavelength with different illumination doses, the illuminations being adjusted so as to effect under- and over-illumination, i.e. mask structures are imaged with dimensions which are greater than the nominal measure up to dimensions which are smaller than the nominal measure. After the illumination, the wafer is subjected to a post-exposure bake by baking it at 110° C. for 60 s on the hotplate. Thereafter, the layer is developed with an aqueous 2.38% tetramethylammonium hydroxide solution at 23° C. for 60 s and the wafer is then flushed with DI water. The development detaches the previously illuminated regions.

The results are compiled in Table 3 below:

TABLE 3

| Resist | DTP [mJ/cm$^2$][1] | Dark attrition [nm/min][2] | Solubility [d][3] |
|---|---|---|---|
| No. 1 | 78 | 18 | >15 |
| No. 2 | 82 | 15 | 10 |
| No. 3 | 54 | 25 | >15 |
| No. 4 | 67 | 21 | >15 |
| No. 5 | 51 | 29 | >15 |
| No. 6 | 46 | 31 | >15 |
| No. 7 | 59 | 35 | >15 |
| No. 8 | 61 | 25 | >15 |
| No. 9 | 55 | 32 | >15 |
| No. 10 | 54 | 29 | —[4] |
| No. 11 | 45 | 32 | 5 |

[1] Dose to print (DTP): minimum illumination energy required to transfer the structures of the mask to the resist in identical dimensions after development

[2] The dark attrition reports the resist layer thickness detached in the unilluminated regions in the course of development per unit time

[3] Time in days for which a 5% by weight solution of the PAC used in the resist in PGMEA remains stable at 25° C. until the first visible cloudiness appears

[4] not completely soluble

In comparative lithographic tests between the inventive compounds and two known comparative specimens, no disadvantageous properties are found with regard to the lithography. In addition to comparable light sensitivities (see Table 3), the dissolution capacity and the clean development behaviour of all specimens are also the same within a narrow range, but solutions of the inventive compounds (I) have significantly longer storage stability (see Table 3, column 4).

The invention claimed is:

1. A compound of the formula (I)

where the symbols and indices are each defined as follows:

A is A', R or OR, where R is a straight-chain or branched (C$_1$-C$_8$)-alkyl group or (C$_3$-C$_3$)-cycloalkyl;

A' is the same or different and is

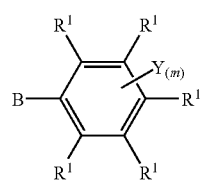

B is a bond, —O—, —C(O)—O—, —O—C(O)—, —C(O)—O—CH$_2$—CH(OH)—CH$_2$—O— or —CH$_2$—CH(OH)—CH$_2$—O—C(O)—;

R$^1$ is H or OH;

m is 2, 3 or 4;

Y is

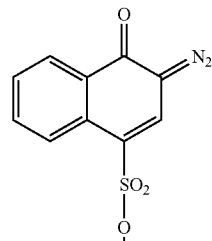

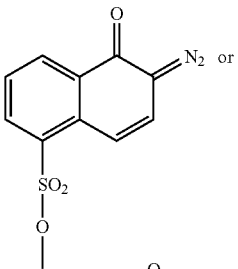

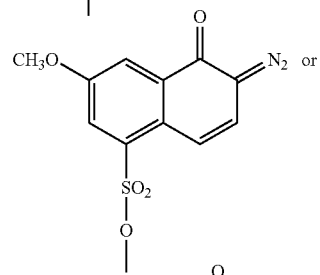

n is a positive rational number $\geq 3$ and $\leq 80$;

E is —CH$_2$—CHR$^2$—O—, —O—CHR$^2$—CH$_2$— or —(CH$_2$)$_r$—O—, —O—(CH$_2$)$_r$—;

R$^2$ is H or CH$_3$; and r is 1 or 4.

2. The compound of formula (I) according to claim 1, where

Y is

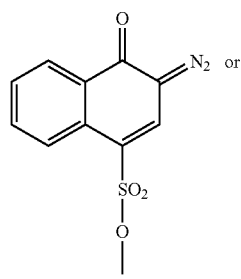

-continued

Y is

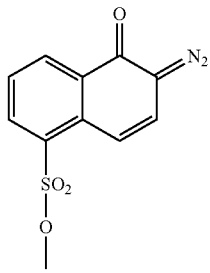
(III)

3. The compound of formula (I) according to claim 1, where the symbols and indices in the formula (I) are each defined as follows:

A is A', R or OR, where R is a straight-chain or branched ($C_1$-$C_8$)-alkyl group;

B is a bond, —O—, —O—C(O)—, —C(O)—O—, C(O)—O—CH$_2$—CH(OH)—CH$_2$—O or —CH$_2$—CH(OH)—CH$_2$—O—C(O);

$R^1$ is H or OH;

m is 2 or 3;

Y is

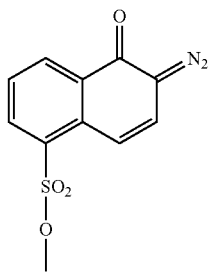
(III)

$n \geq 5$ and $\leq 20$ and

E is —CH$_2$—CH(CH$_3$)—O, —CH$_2$—CH$_2$—O, —O—CH$_2$(CH$_3$)—CH$_2$—, —O—CH$_2$—CH$_2$—, —CH(CH$_3$)—CH$_2$—O, —O—CH$_2$—CH(CH$_3$)— or (CH$_2$)$_4$—O— or —O—(CH$_2$)$_4$—.

4. The compound of formula (I) according to claim 1, where the symbols and indices in the formula (I) are each defined as follows:

A is A', a straight-chain or branched ($C_1$-$C_4$)-alkyl group;

B is a bond, —C(O)—O—, C(O)—O—CH$_2$—CH(OH)—CH$_2$—O— or —CH$_2$—CH(OH)—CH$_2$—O—C(O)—;

$R^1$ is H or OH;

m is 2 or 3;

Y is

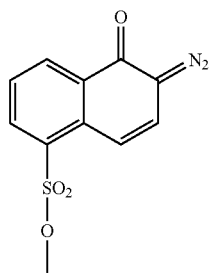
(III)

n is $\geq 5$ and $\leq 15$ and

E is —O—CH$_2$—CH$_2$—, —CH$_2$—CH$_2$—O—, —O—CH(CH$_3$)—CH$_2$—, —O—CH$_2$—CH(CH$_3$)—, CH(CH$_3$)—CH$_2$—O— or —CH$_2$—CH(CH$_3$)—O—.

5. A process for preparing a compound of formula (I) according to claim 1 by reacting a compound of the formula (I)' in which

A' is

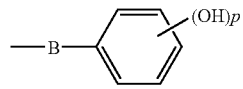

p is 1, 2, 3, 4 or 5 and the remaining symbols and indices are each as defined in formula (I), in an organic solvent in the presence of a base, with at least one compound from the group of 2,1-diazonaphthoquinone-4-sulphonyl chloride, 2,1-diazo-naphthoquinone-5-sulphonyl chloride, 7-methoxy-2,1-diazonaphthoquinone-4- and 5-sulphonyl chloride.

6. A photoresist composition comprising a) a light-sensitive component comprising one or more compounds of the formula (I) according to claim 1 and b) a film-forming, base-soluble component.

7. A process for the structured coating of a substrate by a) coating a substrate with a film of a photoresist composition according to claim 6, b) illuminating the photoresist film formed through a photomask, c) baking the illuminated photoresist film and d) developing the baked, illuminated photoresist film with an alkaline developer.

8. A substrate coated with a photoresist composition according to claim 6.

9. The compound of claim 1, where A is A'.

10. The photoresist composition of claim 6, where the film forming, base soluble component is a novolak resin.

\* \* \* \* \*